(12) United States Patent
Wood et al.

(10) Patent No.: US 10,736,703 B2
(45) Date of Patent: Aug. 11, 2020

(54) DEPLOYABLE POLYGONAL MANIPULATOR FOR MINIMALLY INVASIVE SURGICAL INTERVENTIONS

(71) Applicant: Carnegie Mellon University, Pittsburgh, PA (US)

(72) Inventors: Nathan Wood, Pittsburgh, PA (US); Cameron Riviere, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 1072 days.

(21) Appl. No.: 14/725,848

(22) Filed: May 29, 2015

(65) Prior Publication Data

US 2015/0342688 A1 Dec. 3, 2015

Related U.S. Application Data

(60) Provisional application No. 61/997,378, filed on May 29, 2014.

(51) Int. Cl.
| | | |
|---|---|---|
| A61B 34/00 | (2016.01) | |
| A61B 17/34 | (2006.01) | |
| A61B 8/12 | (2006.01) | |
| A61B 17/00 | (2006.01) | |
| A61B 17/02 | (2006.01) | |
| A61B 8/00 | (2006.01) | |
| A61B 17/30 | (2006.01) | |
| A61B 34/20 | (2016.01) | |
| A61B 90/00 | (2016.01) | |
| A61B 90/30 | (2016.01) | |

(52) U.S. Cl.
CPC .......... *A61B 34/71* (2016.02); *A61B 17/3478* (2013.01); *A61B 8/12* (2013.01); *A61B 8/4209* (2013.01); *A61B 8/4477* (2013.01); *A61B 90/361* (2016.02); *A61B 2017/00243* (2013.01); *A61B 2017/00247* (2013.01); *A61B 2017/0243* (2013.01); *A61B 2017/308* (2013.01); *A61B 2017/3409* (2013.01); *A61B 2034/2051* (2016.02); *A61B 2090/306* (2016.02); *A61B 2090/309* (2016.02); *A61B 2090/3966* (2016.02)

(58) Field of Classification Search
None
See application file for complete search history.

(56) References Cited

U.S. PATENT DOCUMENTS

| 5,906,607 A | 5/1999 | Taylor et al. |
|---|---|---|
| 6,589,166 B2 | 7/2003 | Knight et al. |

(Continued)

OTHER PUBLICATIONS

Degani, Amir et al., "Highly Articulated Robotic Probe for Minimally Invasive Surgery" Proceedings of the 2006 IEEE International Conference on Robotics and Automation, May 2006: 4167-4172.

(Continued)

*Primary Examiner* — Angela M Hoffa
*Assistant Examiner* — Farouk A Bruce
(74) *Attorney, Agent, or Firm* — The Webb Law Firm

(57) ABSTRACT

A polygonal manipulator device for surgical interventions of the heart and other smooth organs is provided. A system implementing the device also is provided along with methods of use of the device and system. Methods of use of the device and system, such as for minimally-invasive cardiac intervention methods, are provided.

40 Claims, 13 Drawing Sheets

(56) References Cited

U.S. PATENT DOCUMENTS

| | | | |
|---|---|---|---|
| 7,201,716 B2 | 4/2007 | Boone et al. | |
| 8,162,925 B2 | 4/2012 | Riviere et al. | |
| 2002/0095139 A1* | 7/2002 | Keogh | A61B 17/0206 606/1 |
| 2007/0123748 A1* | 5/2007 | Meglan | A61B 1/00149 600/104 |
| 2011/0144572 A1* | 6/2011 | Kassab | A61M 25/0084 604/35 |
| 2012/0078061 A1* | 3/2012 | Calafiore | A61B 17/0206 600/229 |
| 2012/0265082 A1* | 10/2012 | Hjelle | A61B 5/107 600/508 |

OTHER PUBLICATIONS

Grundeman, Paul F. et al., "Ninety Degree Anterior Cardiac Displacement in Off-Pump Coronary Artery Bypass Grafting: the Starfish Cardiac Positioner Preserves Stroke Volume and Arterial Pressure" Ann. Thorac Surg, 2004; 78: 679-85.

Ota, Takeyoshi., et al., "Minimally Invasive Epicardial Injection Using a Novel Semiautonomous Robotic Device" NIH Public Access Author Manuscript, 2008; 118: S115-S120.

Patronik Nicholas A., et al., "A miniature Mobile Robot for Navigation and Positioning on the Beating heart" IEEE Trans Robot., Oct. 2009; 25(5) 1109-1124.

Scott N.A. et al., "Systematic Review of Beating Heart Surgery with the Octopus Tissue Stabilizer" Eur. J. of Cardiothoracic Surg. 2002; 21: 804-17.

\* cited by examiner

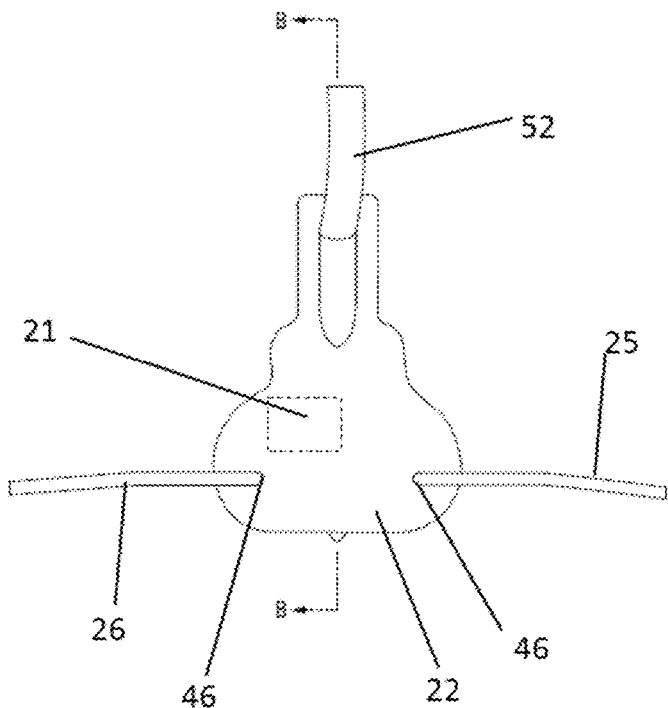
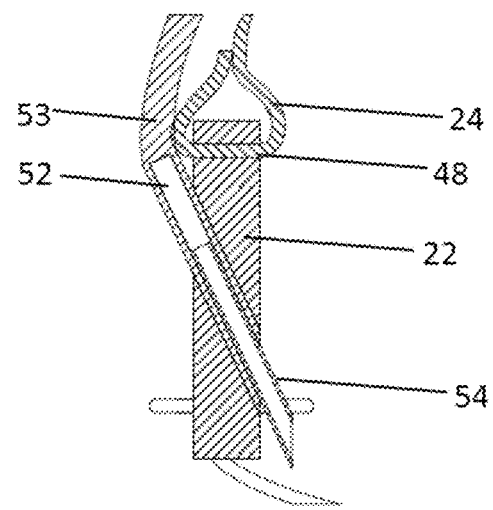
*Fig. 6A*     *Fig. 6B*
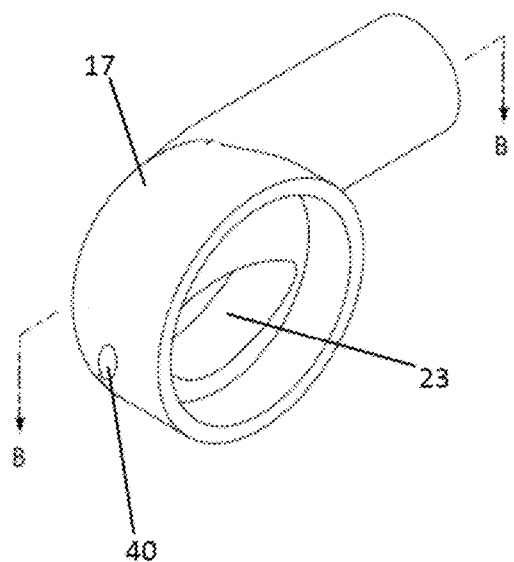
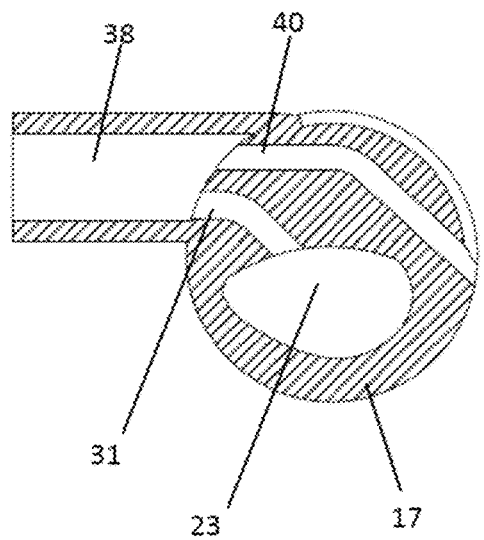
*Fig. 7A*     *Fig. 7B*

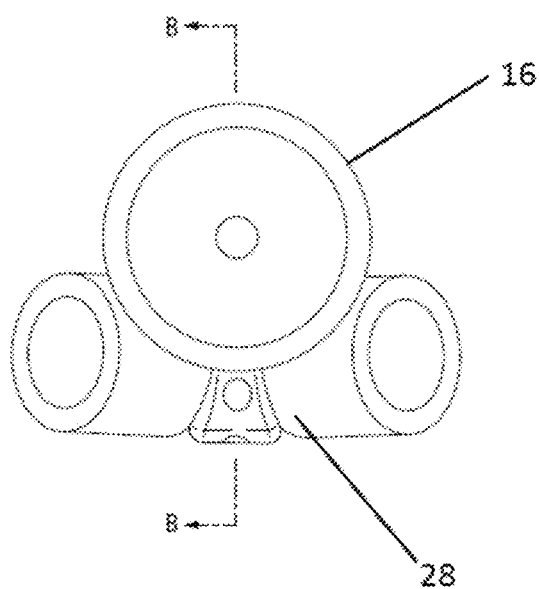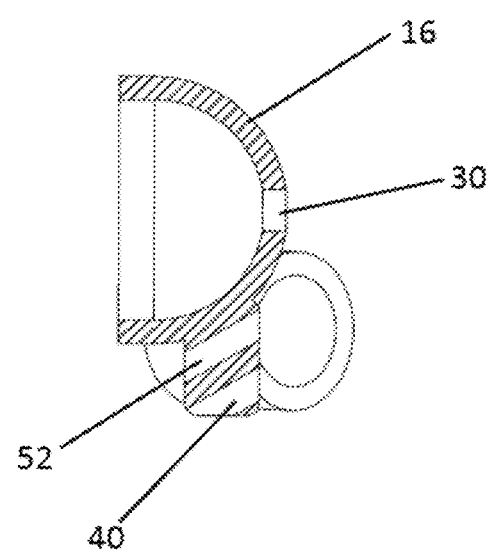
*Fig. 8A*     *Fig. 8B*

DEPLOYABLE POLYGONAL MANIPULATOR FOR MINIMALLY INVASIVE SURGICAL INTERVENTIONS

CROSS REFERENCE TO RELATED APPLICATIONS

The present application claims the benefit of U.S. Provisional Application Ser. No. 61/997,378, filed May 29, 2014, the entire disclosure of which is hereby incorporated by reference.

BACKGROUND

Field of the Invention

The present disclosure relates generally to a device for minimally invasive surgical interventions. More particularly, the present disclosure relates to a deployable polygonal manipulator device, system, and method of using the system for performing minimally invasive surgical interventions on the heart.

Description of Related Art

Several promising gene therapies for heart failure are currently under development, but they lack effective means for delivery to the myocardium. Homogeneity of gene expression is important in order to avoid arrhythmia; therefore, a large number of small injections over a relatively large area needed. The large number of injections must be placed accurately, and preferably while the heart is beating in order to avoid the morbidity associated with cardiopulmonary bypass.

Cardiac surgery may be performed in an open manner in which the heart is exposed through the chest cavity or by a minimally invasive technique. Minimally invasive methods possess significant advantages over open procedures including decreasing both the risk of infection and recovery time for patients. Thoracoscopy is frequently used as a means to access the heart in a minimally invasive manner. Although thoracoscopic techniques are preferable to open heart surgery, they are still traumatic in that the lung must be deflated in order to gain the necessary access to the heart. Additionally, the rigidity of the tools limits access to certain portions of the heart. Moreover, stabilization devices are required in order to enable interventions on the beating heart.

To overcome some of these problems, U.S. Pat. No. 8,162,925 proposed an inchworm-style surgical robot having two suction bodies to adhere to the heart, thereby placing the robot in a stabilized, fixed frame of reference with respect to the moving heart while performing a surgical intervention. The inchworm device is capable of delivering therapies to all surfaces of the heart to which it attaches by crawling from one intervention site to the next. However, for surgical procedures such as cardiac ablation and gene therapy procedures that require more than one intervention over a relatively large area, the necessitated crawling motion is an inefficient process that can only be accomplished by alternating the suction force exerted by the two suction bodies. This time-consuming process increases the length of the surgical procedure thereby increasing the chances of error and surgical complications.

For these reasons, a need exists for a device that will provide both the stable platform necessary to perform a minimally invasive surgical intervention on a moving, smooth organ such as the heart, without sacrificing the device's ability to efficiently perform repeated interventions.

SUMMARY

The present invention overcomes the problems associated with earlier devices because the deployable polygonal manipulator device provides a stable platform for stabilizing the device on a smooth surface and a separate mechanism to quickly and accurately position a working head of the device to efficiently perform repeated interventions. The devices, systems, and methods described herein facilitate minimally invasive surgical interventions. Once deployed, the device described herein is able to efficiently perform a series of interventions on a smooth and moving internal organ.

Provided herein is a deployable manipulator device. According to one embodiment, the device includes a support structure having a plurality of support arms having distal ends and a junction, and which are collapsible between a delivery configuration where the arms are collapsed, permitting delivery of the device through a cannula, and an expanded, deployment configuration. The device further comprises, at least three suction bases, with at least two of the suction bases being located on the support arms, for example, at distal ends of the support arms, so that a distance between two suction bases located on different support arms is greater in the deployment configuration as compared to the delivery configuration. The device comprises a working head, such as a tissue ablator or an injector, and at least three cables connected to the working head and passing through cable guides, such as channels, optionally comprising pulleys, located at three points on the support structure. The cable guides are non-collinear when the device is deployed, forming a triangle with the cable guides forming vertices of the triangle and with the working head located within the triangle. In one example, the cable guides are integral with or attached to the at least three suction bases. According to one embodiment, the support structure comprises two flexible support arms joined at a junction, with one suction base at the junction and one suction base being secured to each of the two support arms distal to the junction, for example at distal ends of each of the arms, and each of the suction bases comprising a cable guide through which one of the cables attached to the working head passes.

A system for using the deployable manipulator device in performing a surgical intervention is also provided. The system includes the deployable manipulator device as described herein, a vacuum source to provide negative pressure to the at least three suction bases, an actuator to control the positioning of the working head by coordinated movement of the cables attached to the working head, a cannula through which the device is delivered, and an electronic control system for controlling at least the actuator and the vacuum source thereby controlling the position of the working head and the negative pressure (suction) at the at least three suction bases.

A method is provided for performing a surgical intervention at one or more intervention sites in a patient using a deployable manipulator device and system as described herein. The method includes, introducing the device into a patient through an incision, positioning a support structure of the device over a specified location of a target organ, attaching the support structure to the target organ, positioning a working head over an intervention site located at a specified location of the target organ, performing the surgical intervention, and retrieving the device upon completion of the surgical intervention.

In one embodiment, a deployable manipulator device is provided for surgical interventions. The device comprising: a) a support structure being transitionable between a delivery configuration and a deployment configuration, comprising: at least three suction bases, each comprising a chamber, a first opening and a second opening attached to a vacuum line, wherein a distance between at least two suction bases is greater in the deployment configuration as compared to the delivery configuration; and at least three cable guides at three non-collinear points on the support structure when in the deployment configuration, wherein a distance between at least two of the cable guides is greater in the deployment configuration as compared to the delivery configuration; b) a working head; and c) three or more cables connected to the working head and passing through the three cable guides, wherein the cables move within the cable guides to move the working head between the suction bases.

In another embodiment, the device comprises: a) a support structure comprising: a plurality of support arms each being attached at a proximal end to a connector and having distal ends, wherein the support arms can be manipulated between a delivery configuration and a deployment configuration where distal ends of the arms are separated by a greater distance in the deployment configuration; at least three suction bases comprising a chamber, a first opening and a second opening attached to a vacuum line, with at least two of the suction bases being attached to different support arms so that a distance between the at least two suction bases located on different support arms is greater in the deployment configuration as compared to the delivery configuration; and at least three cable guides at three non-collinear points on the support structure in its deployed configuration, with at least two of the cable guides being attached to different support arms so that a distance between the at least two cable guides located on different support arms is greater in the deployment configuration as compared to the delivery configuration; b) a working head; and c) three or more cables connected to the working head and passing through the three cable guides, wherein the cables move within the cable guides to move the working head between the suction bases.

In certain embodiments, the plurality of support arms are made from a flexible material or a resilient material. When the plurality of support arms are flexible, the device might further comprise an introducer attached to one or more of the suction bases to facilitate placement of the suction bases. In one embodiment, each of the support arms have a length extending from a distal end of the support arm to a proximal end of the support arm, wherein at least one of the support arms has greater flexibility along its length in one direction as compared to a direction perpendicular to the one direction. In other embodiments, the arms are inflexible or have limited flexibility, and they are hinged at their proximal end. In such a case, the device in one embodiment further comprises at least one spring disposed at a joint located between the plurality of support arms to bias at least a portion of the plurality of support arms apart from one another.

In one embodiment, the at least three suction bases include a proximal suction base and a plurality of distal suction bases, wherein each of the distal and proximal suction bases comprise one of the at least three cable guides through which one of the at least three cables passes. In one embodiment, the device comprises an introducer attached to the proximal base and each of the distal bases.

In one embodiment, the support structure includes three suction bases that are triangularly spaced apart when the support arms are in the deployed configuration. In another embodiment, at least one of the cable guides are integral with a suction base. The device optionally comprises a vacuum source connected to the at least three suction bases by a vacuum line fluidly connecting the vacuum source to each of the at least three suction bases, which produces a negative pressure in each of the suction bases to hold the device in place on an anatomical structure. To facilitate deployment, e.g., within the thoracic cavity via a subxyphoid route, the device in one embodiment comprises one or more introducer elements secured to one of the at least three suction bases. The introducer element(s) may be permanently affixed to the base or may be releasably attached by any useful fastener configuration. The introducer element may be a flat, elongated metal or polymer strip bending in substantially only one plane.

To assist in precise delivery and action of the device, the device in one embodiment comprises one or more electromagnetic positioning sensors, cameras, ultrasound probes and/or fiberscopes. Radiopaque elements are incorporated in one or more of the suction bases and/or working head to facilitate visualization of the position of the device when in use. In one embodiment, the working head comprises a retractable needle, which can deliver a fluid supplied from a tube attached to the needle. A needle array, that is, a plurality of retractable needles may be provided on the working head. In another embodiment, the working head comprises a mechanical, electrical, or laser tissue ablation head. In one embodiment, the ablator comprises a blade, laser or radiofrequency ablator.

Also provided herein is a system for performing a surgical intervention. The system comprises: the deployable manipulator device as described above and herein; a vacuum source to provide negative pressure to the at least three suction bases; an electronic control system for at least controlling the positioning of the working head; and an actuator to control the positioning of the working head by independently controllably pulling or releasing each of the cables, thereby positioning the working head. In one embodiment, the actuator comprises a plurality of bobbins around which proximal ends of the cables are wrapped, wherein the bobbins are connected to a servo motor, and the cables are pulled or released by rotation of the bobbins.

Also provided herein is a method for performing a surgical intervention using a manipulator device. The method comprises introducing the device according to any embodiment described herein into a patient through an incision; positioning the support structure of the device over a location of a target organ; attaching the support structure to the target organ by applying a vacuum to the suction bases; positioning the working head over an intervention site located at the location of the target organ; performing the surgical intervention using the working head; and retrieving the device upon completion of the surgical intervention. Movement of the working head and/or placement of the device may be monitored by any effective real-time medical imaging method, such as by fluoroscopy.

BRIEF DESCRIPTION OF THE DRAWINGS

The present invention will now be described in further details with reference to the accompanying figures, in which:

FIG. 6A is a top view of an injector head component of a deployable polygonal manipulator device described herein.

FIG. 6B is a cross-sectional view taken along B-B of FIG. 6A.

FIG. 7A is a perspective view of a distal suction base of a deployable polygonal manipulator device as described herein.

FIG. 7B is a cross-sectional view taken along B-B of FIG. 7A.

FIG. 8A is a bottom view of an integral suction base and connector of a deployable polygonal manipulator device as described herein.

FIG. 8B is a cross-sectional view taken along B-B of FIG. 8A.

DETAILED DESCRIPTION

For purposes of the description hereinafter, spatial orientation terms relate to the embodiment of the invention, as it is oriented in the accompanying drawing figures. In the context of the device described herein, "distal" refers to a direction away from a user of the device, such as a surgeon, while "proximal" is the opposite of distal, and refers to a direction towards a user of the device. Further, it is to be understood that the invention may assume many alternative variations and embodiments, except where expressly specified to the contrary. It is also to be understood that the specific embodiments of the device, system, and method illustrated in the accompanying drawing figures and described herein are simply exemplary embodiments of the invention. As used herein, "a" or "an" refers to one or more.

Figure 1:
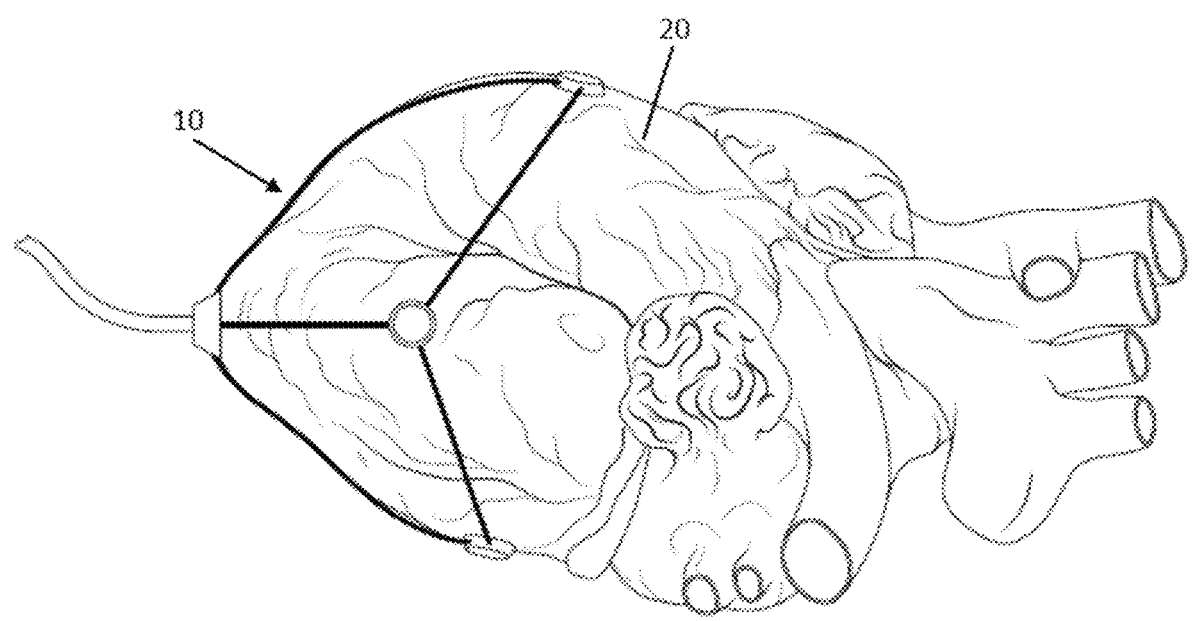
FIG. 1 is a perspective view of a deployable polygonal manipulator device as described herein, attached to a heart.
Figure 2:
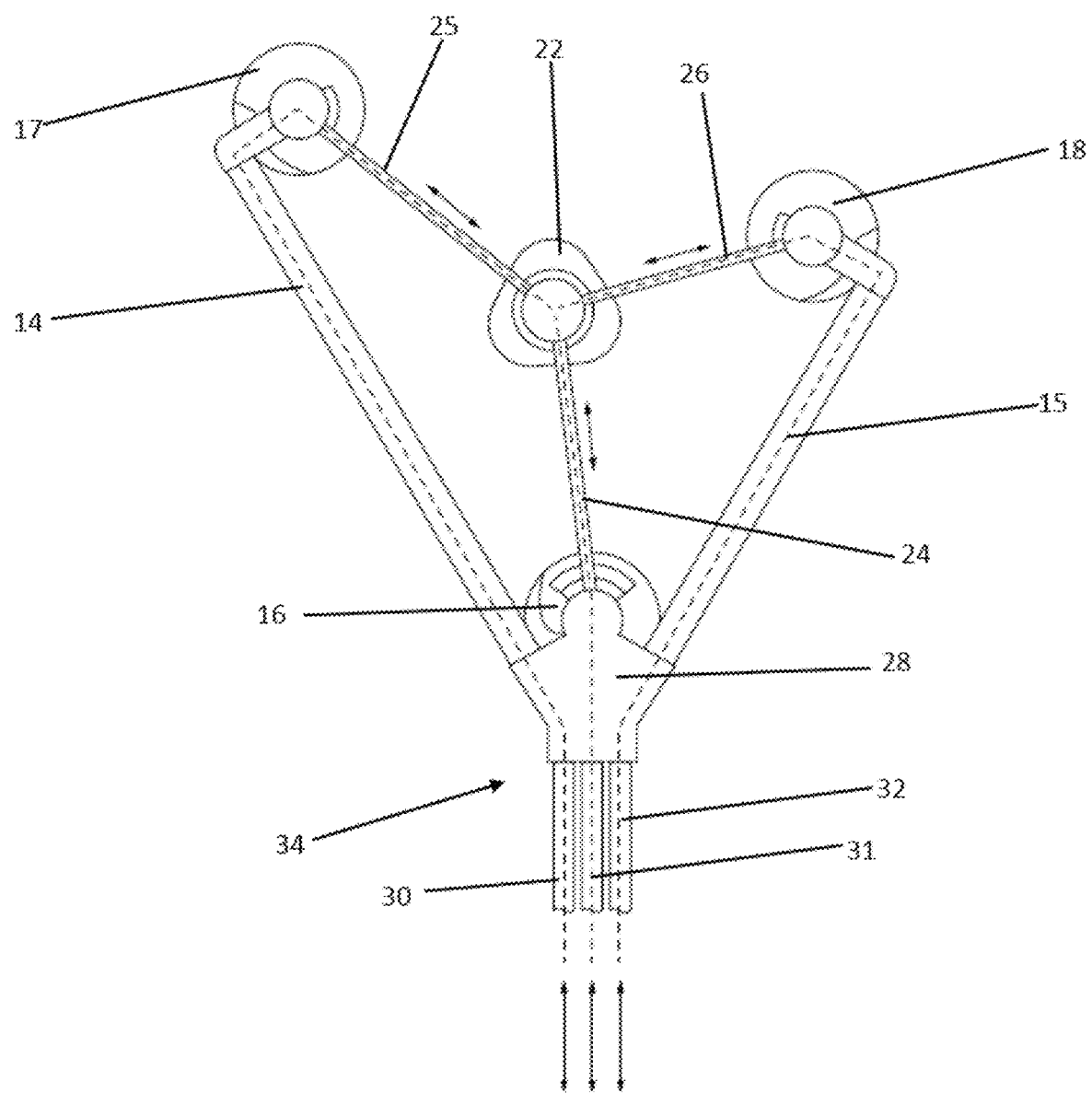
FIG. 2 is a top view of the polygonal manipulator device as described herein in an expanded, deployment configuration.
Figure 3:
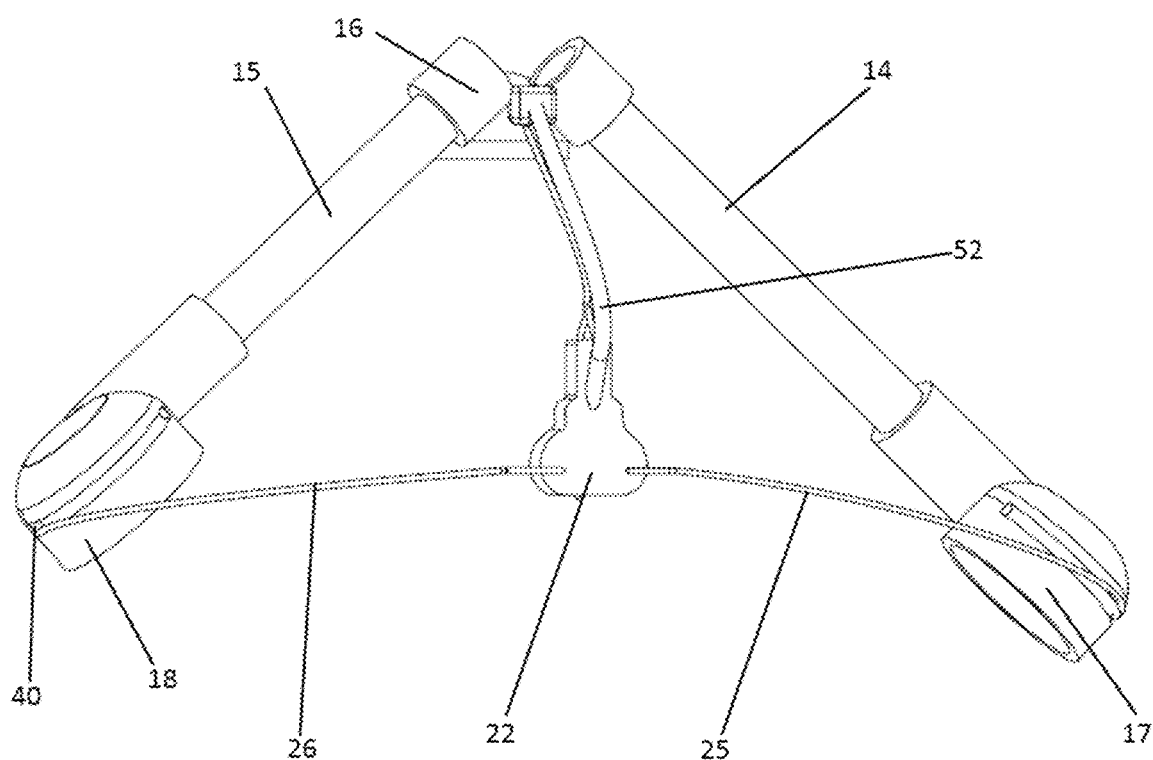
FIG. 3 is a perspective view of a polygonal manipulator device as described herein in an expanded, deployment configuration with an injection head and injection sheath.

FIGS. 1-3 depict one non-limiting embodiment of a device as described herein. In reference to FIGS. 1-3, a deployable polygonal manipulator device 10 for surgical interventions includes a support structure 12, comprising a first arm 14, a second arm 15, a first suction base 16, a second suction base 17, and a third suction base 18. First suction base 16 is attached to connector 28 to which arms 14 and 15 are attached. Suction bases 16, 17, 18, are used to adhere the device 10 to a surface of a target organ, such as a heart 20, as depicted in FIG. 1. Suction bases 16, 17, 18, comprise a chamber, an opening for contacting a surface, such as a heart surface, and a vacuum line, permitting attachment to a vacuum source, such as a vacuum pump or vacuum chamber or manifold that can be attached to and evacuated by a vacuum pump. The polygonal manipulator device 10 further includes a working head 22 and cables 24, 25, 26, each cable being attached to the working head and independently passing through an opening or passage in each of the suction bases 16, 17, 18, respectively (cable guide 40 depicted in FIGS. 3 and 7B). The cables 24, 25, and 26 pass through openings in suction bases 16, 17, 18 and into and through a cable guide, so that tension on cables 24, 25, 26, causes movement of the working head 22 between the suction bases 16, 17, and 18. As used herein, a "cable guide" refers to a passage, hole, opening, ring, etc. through which a cable passes and is able to move freely, and can be a simple ring or tubular passage, or may include a pulley structure (not shown) engaging the cable to reduce friction on the cable. A cable guide may be lined or coated with a lubricant, such as a polytetrafluoroethylene (PTFE, e.g., TEFLON®) tube or coating. The positioning of the working head 22 is rapidly transitionable by independent pulling or releasing lengths of each of cables 24, 25, and 26 from a position proximal to the cable guide.

As used herein, a cannula is a hollow tube used to introduce an object or liquid into a body. The cannula may have any suitable diameter for use and deployment of a device as described herein. A "trocar" is a specialized cannula that is often used in laparoscopic surgery, and includes at least a cannula (tubular) portion.

Figure 4A:
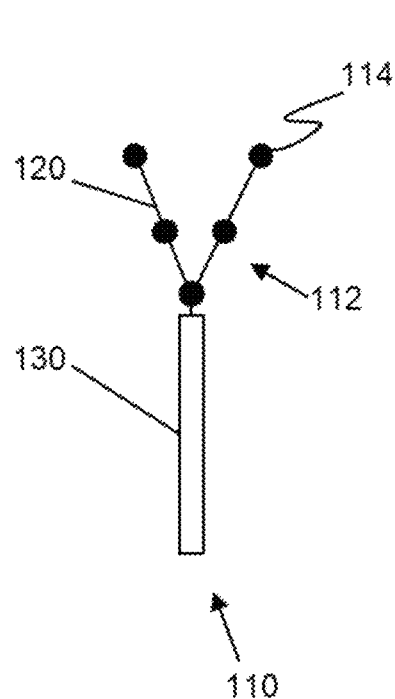
FIGS. 4A-C are schematic drawings of alternative configurations for the polygonal manipulator device.
Figure 4B:
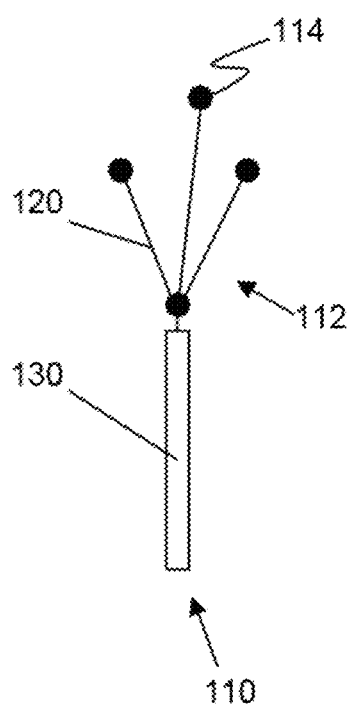
Figure 4C:
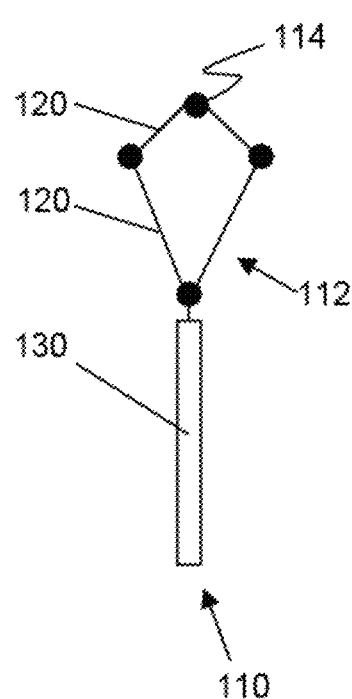

In one embodiment, as shown in FIG. 2, the polygonal manipulator device 10 includes two distal suction bases 17 and 18 and one proximal suction base 16 at a junction between arms 14 and 15. FIGS. 4A-4C depict, schematically, exemplary alternate configurations of the device 10 depicted in FIGS. 1-3, showing only relative orientation of flexure arms 120 of the support structure 112, suction bases 114 and cannula 130 for deployment of the device. As indicated, the support structure 12 may include more than three suction bases. The number of suction bases may be larger than the number of cables. In the embodiment shown in FIGS. 1-3, three cables are used to control the position of the working head. However, three cables, secured at different points on the support base 112 shown in FIG. 4A, and having five suction bases 114, could be used to position the working head.

Figure 5:
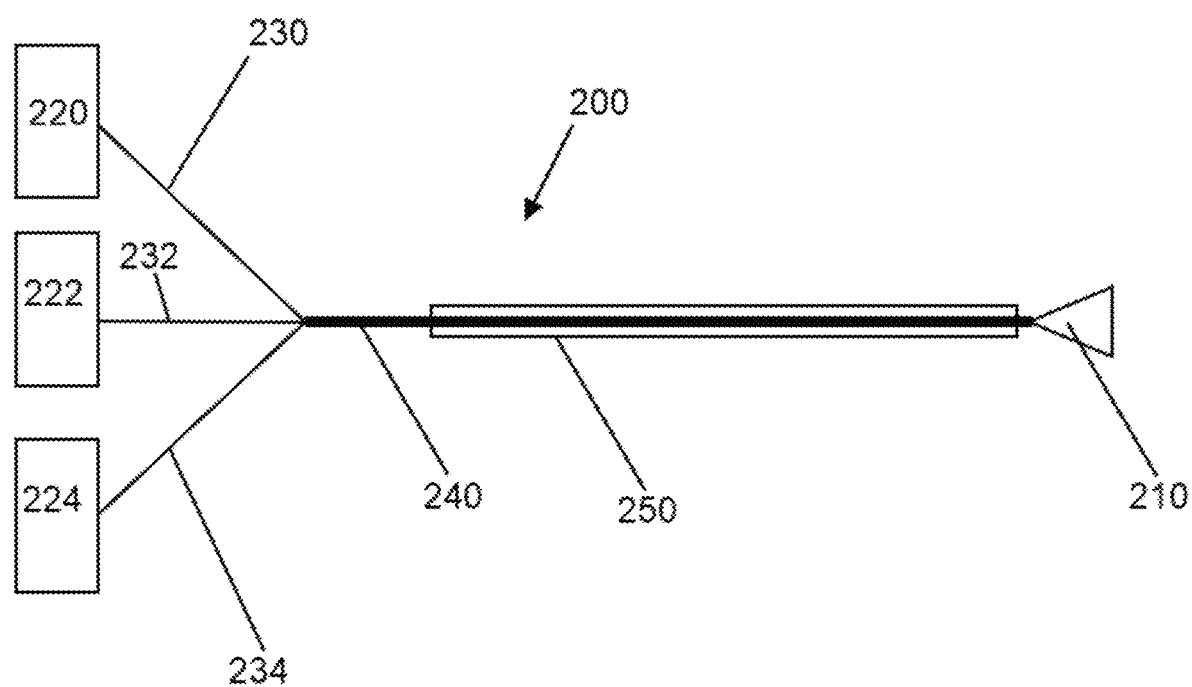
FIG. 5 is a schematic drawing of a system for using a polygonal manipulator device as described herein.

Also provided herein is a system comprising the above described device, in any embodiment described herein, along with delivery and control elements thereof. In FIG. 5, system 200, shown schematically, comprises a deployable polygonal manipulator device 210, essentially as disclosed, for example, in FIGS. 1-3 (device 10) and FIGS. 4A-4C (device 110), comprising a support structure, including arms, suction pads, cables and a working head as described herein. Control of movement of the working head is achieved via actuator 220, which is any useful mechanism for controllably retracting (e.g. pulling) and releasing cables of the device 210, to independently elongate or decrease the length of each of the cables between the actuator and the working head. The actuator 220 controls the position of the working head within the device 210, and thus controls the at least three cables independently as further described below. Cables 230, though depicted as a single line for simplicity, comprises the at least three controller cables as described above. Vacuum unit 222 represents a vacuum unit, such as a vacuum pump to which one or more vacuum lines 232 connect the vacuum pump to each suction base 114. A "vacuum line" is a tube or passage within a structure that can be used to fluidly connect a vacuum to a structure such as the suction bases described herein. A variety of suitable vacuum lines are commercially available, such as Tygon® suction lines. A number of vacuum lines 232 equal to the number of suction bases 114 in the device 210 may be present, with individual controls, e.g., solenoid valves, within the vacuum unit 222. Alternately, one or more vacuum lines 232 may include distal branches at some point proximal to the suction pads so that the suction of more than one suction pad is controlled from a single vacuum line 232. In the depicted embodiment, a working head control 224, for the working head is provided.

A "working head" refers herein to a structure comprising a device having a structure that affects tissue in some manner, such as an injector, an ablation head, which can be, e.g., a laser ablator, an electrical ablator, such as a radiofrequency ablator or a thermal ablator, or a mechanical ablator such as a rotating burr or cutter. Other functional structures include, for example and without limitation: an ultrasound probe, camera (e.g., a suitable charge-coupled device (CCD) and lens combination, with optional lighting from, e.g. an LED or fiber optic cable) and a fiberscope, which optionally may be combined with ablation or injection mechanisms in the device and/or the working head to permit visualization of local tissue/anatomical structures. In the case of the working head being an ablation head, the control is a power source and controls for manipulating the cutting action of the ablation head. Where the working head is an injector, e.g., as depicted in FIGS. 6A and 6B, in one embodiment the working head control 224 comprises an actuator for motion of a needle in the working head, e.g., for controlling reciprocation of the needle, including retraction and depth of the needle at the working head, and independently comprises a pump, such as a peristaltic pump, for delivering a liquid from a reservoir, through a delivery tube 234, such as a conduit 53 of an injection sheath 52 and through a needle 54 as depicted in FIG. 6B. The liquid is stored in a suitable vessel, which is fluidly connected to the needle, e.g., by suitable tubing. The actuator 220, vacuum unit 222 and working head control 224 are computer-controlled in order to coordinate action of each independently.

The implementation of the automated tasks, such as control of the positioning of the working head, application of suction to the suction bases, and ablation or injection activities, can be readily achieved by a person of ordinary skill in computer programming. Examples below describe one non-limiting embodiment of a useful computer system. A computer, or computer system comprises at a minimum a processor, memory and instructions (e.g., software) stored on a non-transitory medium. Instructions include a suitable operating system, and instructions for carrying out the functions described herein.

FIGS. 7A and 7B depict an embodiment of suction base 16, 17, 18 useful in the methods described herein. With reference to FIGS. 2, 7A and 7B, a negative pressure (suction force) is be applied to a vacuum chamber 23 disposed within an open end of exemplary suction base 17 via vacuum line 31, which extends through connector 28 located at the junction between arms 14 and 15, at proximal end 32 of the device 10. Vacuum lines 30, 31 and 32, connected to the proximal suction base 16 and the distal bases 17 and 18 pass through connector 28. To prevent particles from being suctioned into the vacuum chamber 23 and clogging the vacuum lines, a mesh netting or filter (not shown) optionally covers the vacuum chamber 23 to keep out particles. Alternately, or in addition to having mesh nettings or filters at each of suction bases 16, 17, 18 an optional filter (not shown) may also be provided in-line with one or more of the vacuum lines 30, 31 and 32, to remove fluids and small particles that passed through the mesh netting.

Elements of the device, such as device 10 or 110 can be manufactured by any suitable method for manufacturing plastic (polymer) devices, such as by injection molding, molding or 3D printing. In one example, the suction bases 16, 17, 18 are built using a rapid prototyping method, such as 3D printing directly from CAD software.

Figure 9:
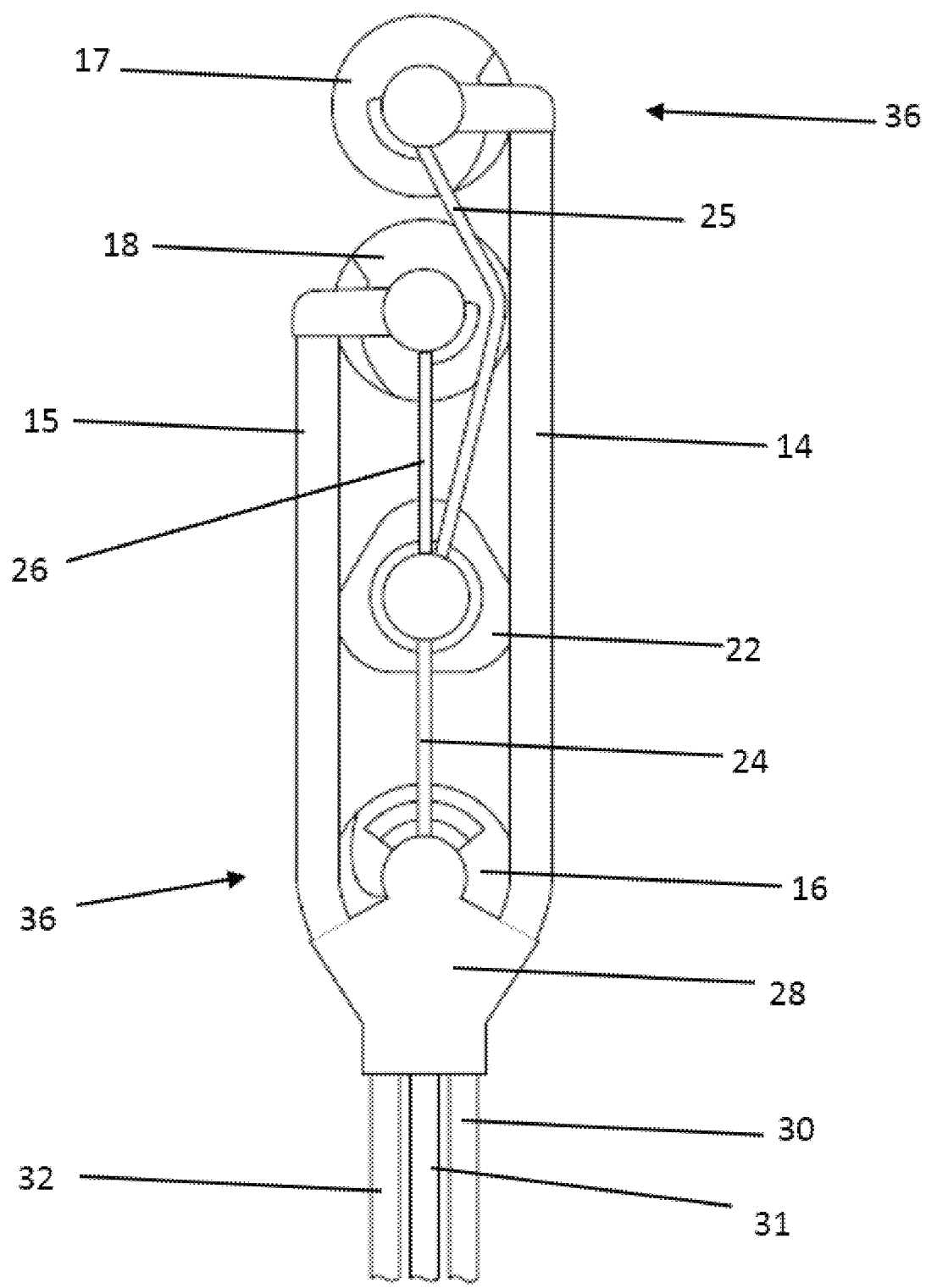
FIG. 9 is a top view of a polygonal manipulator device in a collapsed, delivery configuration.

Flexure arms 14 and 15 extend from the connector 28, as shown in FIG. 2. It is understood that more than two flexure arms may be used. In one embodiment, the proximal suction base 16 forms a joint with the two flexure arms 14 and 15 at the proximal end 34 of the device 10 near the connector 28. As is shown in FIG. 9, the distal suction bases 17 and 18 are connected to a distal end 36 of the two flexure arms 14 and 15. The flexure arms 14 and 15 are configured to be transitionable from a collapsed configuration (as shown in FIG. 9), in which the two flexure arms 14 and 15 are bent at their proximal ends 37 so that they are adjacent and parallel to one another, to an expanded, deployment configuration (e.g., as shown in FIGS. 2 and 4A-4C) in which the distal suction bases 17 and 18 move apart from one another to form a triangular shape.

The flexure arms 14 and 15 are transitionable by either a passive or active method. In one embodiment the flexure arms are manufactured from a resilient material, such as a wire, rubber, e.g., neoprene rubber, or polymer, in which the flexure arms 14 and 15 are bent into the collapsed position by applying an inward force on the distal end 36 of the flexure arms 14 and 15, e.g., by insertion into a cannula. By "resilient" it is meant that the material is able to recoil or spring back into shape after bending, such that a resilient flexure arm can be bent into a compressed configuration, and will spring to the deployed configuration when compression forces are released, such as by deployment from a catheter. When the inward force is released, the resilient flexure arms 14 and 15 return to their natural expanded position. Alternately, one or more torsional spring (not shown) may also be disposed within a joint located between the flexure arms 14 and 15 to bias the flexure arms towards the expanded position. A "spring" is any structure capable of biasing the flexure arms 14 and 15 outwardly and apart from each other. The springs may be manufactured as a metal coil or strip or any other useful material. In one embodiment, illustrated by FIGS. 2 and 9, depicting two embodiments having alternate arm arrangements, one of the flexure arms 14 is longer than the other flexure arm 15. For example, the longer arm 14 is 25 mm to 100 mm longer than the shorter arm 15, for example in one non-limiting embodiment the longer arm 14 is 100 mm long, while the shorter arm 15 is 75 mm long. Still alternatively, the flexure arms 14 and 15 are transitionable by actuation. For example, a foldable strut (not shown) may be connected between the two distal suction bases 17 and 18 so that the flexure arms 14 and 15 may transition to their expanded triangular shape by pushing the foldable strut into place with a wire (not shown), for example, that would force the strut to straighten out to form a third side of the triangle.

Figures 13A, 13B:
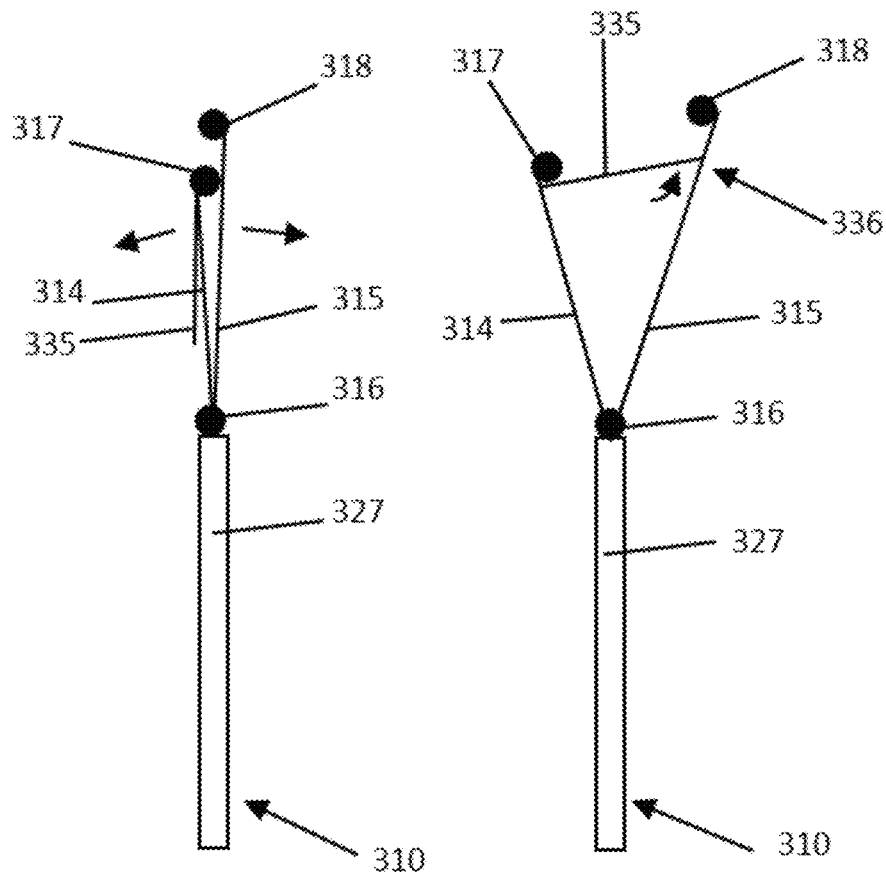
FIGS. 13A and 13B depict alternate embodiments of a polygonal manipulator device as described herein.

In certain embodiments, such as the device as depicted in FIGS. 13A and 13B, discussed below, or other active deployment methods, the arms can be rigid. However, rigid arms prevent compliance of the device to the anatomical structure. This difficulty is solved by having flexible and optionally resilient arms that can better "wrap" about the targeted anatomical structure. The resilient arms described above facilitate deployment and conformity to an anatomical structure. Alternatively, arms that are flexible but not resilient, e.g., passive articulated arms, can also conform to the anatomical structure, although they do not facilitate deployment. Flexible arms also create a difficulty, however, as the flexibility that allows conformity to the heart also impedes accurate positioning of the arms. A solution to this problem is to provide (either passive or active) introducers as described herein, which are manipulators, such as rods, tubes, guide wires or other devices, which can be attached, releasably or not, to distal suction bases, permitting precise positioning of the bases. An introducer may be releasable attached in any manner, for example and without limitation by a combination of a threaded bore and screw for engaging the threaded bore. According to one embodiment, the arms are flexible, but can only flex in substantially one plane, as with a polymeric band analogous to a cable-tie, or a multi-link, articulated metallic band analogous to a typical linked watch band or bicycle chain. This may be accomplished by use of an elongated structure, such as an articulated metallic structure, having a longitudinal axis and a transverse axis perpendicular to the longitudinal axis, corresponding to a width of the structure, and having a plurality of hinged links or segments of any configuration, that permit flexure of the structure, but restrict flexure of the structure to substantially one plane including the longitudinal axis and an axis perpendicular to both the longitudinal axis and the transverse axis. Examples of analogous structures are watch bands or bracelet configurations, as are broadly known.

In yet another embodiment, the support arms are omitted. In one example of this embodiment, in reference to the embodiment depicted in FIGS. 10A-10C, the three suction bases 16, 17 and 18 are each independently attached to introducers 50 and 51, but the arms 14 and 15 are not present, permitting each suction base 16, 17 and 18 to move freely in relation to the other, but constrained by the presence of vacuum tubes and cables attached to each suction base 16, 17 and 18. Vacuum tubes (not shown) are attached to each of the suction bases 16, 17 and 18. Introducers 50 and 51 are used to independently position each of the suction bases 16, 17 and 18 on an anatomical structure, such as a heart.

Cables useful in the device, system and method described herein, can be any cable, cord, thread, string, and can be prepared from metallic, polymeric and/or natural elements. Non-limiting examples of useful cable materials include a NITINOL alloy, polymeric braided or monofilament cords, such as nylon, polyvinylidene fluoride (PVDF), Dacron, polyethylene and ultra-high molecular weight polyethylene (UHMWPE), etc., as are broadly known. With specific reference to FIGS. 7A and 7B, the cables and the vacuum lines are enclosed within a channel 38 and extend from the distal suction bases 17 and 18 to the connector 28 through each of the flexure arms 14 and 15. Each of the channels may be made from polytetrafluoroethylene (PTFE) or any other suitable material capable of defining a channel without compromising the flexure arms 14 and 15 ability to expand or collapse. In one embodiment, flexure arms 14 and 15 comprise a flexible core element, and the flexible core, along with any cables and vacuum lines, are contained within a sheath, which may be a polymeric tube, such as a PTFE tube.

With continued reference to FIGS. 1-3, 7A, and 7B, each cable extends from the cable guide 40 located within each of the distal suction bases 17 and 18 and connecting to the working head 22.

With reference to FIGS. 6A and 6B, the cables 25 and 26 extending from the distal suction base 17 and 18 shown in FIG. 2, are attached at knot locations 46 located near a distal end of the working head 22. Likewise, the cable 24 extending from the proximal suction base 16 is attached at a knot location 48 located near a proximal end of the working head 22. The working head 22 may be modular in nature and may be designed to perform a variety of functions. Examples of working heads may include a discrete injection module and a micro-needle array injection module configured to allow for cell transplantations, gene therapy, drug delivery, an ablation module for atrial ablation, and an insertion tool for pacing electrode placement. Optionally the working head 22 may include an electromagnetic tracker 21 (internal the working head, in phantom), having a coil arrangement configured to generate a magnetic field. Non-limiting examples of electromagnetic trackers include: trakSTAR, Ascension Technology Corp., Shelburne, Vt.; Aurora, Northern Digital Inc., Waterloo, ONT, Canada; and Liberty, Polhemus, Colchester, Vt. A second coil (not shown and external to the device 10) may be used to create a second magnetic field. By processing a waveform indicative of the first and second field, one will be able to calculate the positioning of the working head 22.

Figure 11:
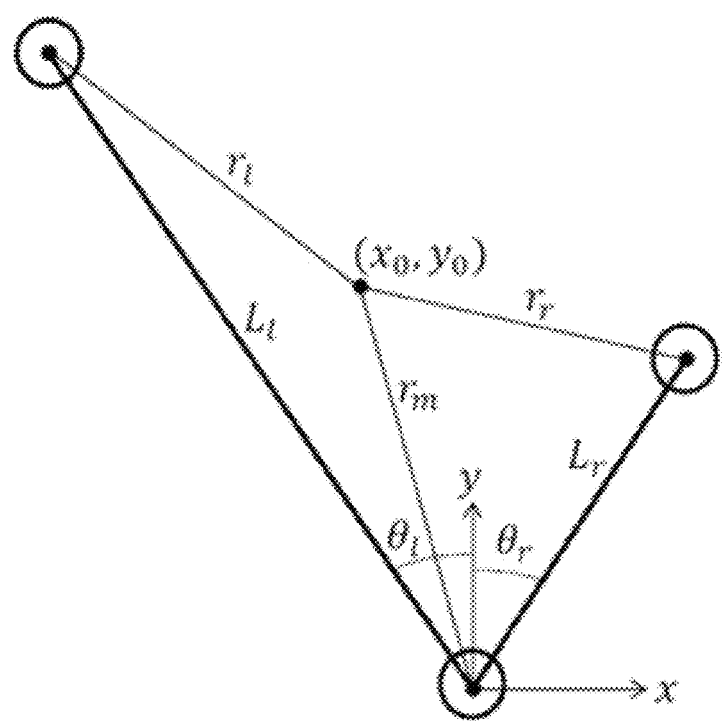
FIG. 11 is a model kinematics of a working head and cables of the polygonal manipulator device as described in the Example.

By manipulating the relative length of the cables 24, 25, 26 as explained hereafter, the positioning of the working head 22 can rapidly and accurately be adjusted. For motion and path planning, a planar approximation may be made. Because the device 10 is a parallel manipulator, no closed form solution is necessary for forward kinematics. However, planar approximation means that the inverse kinematics can be solved by drawing a circle concentric to each suction base 114 and finding the location where each circle intersects, an example of which is shown by FIG. 11. Planning algorithms may be developed from this information that permit a surgeon to draw a path representing a series of injection sites, to which the manipulator can autonomously travel under, as will be explained hereinafter, under minimum-jerk trajectory conditions.

In one embodiment, with reference to FIGS. 3 and 6B, an injection sheath 52 extends from the connector 28 to the working head 22. The injection sheath having a conduit 53 extending from the proximal end of the injection sheath, located at the connector 28, to the distal end of the injection sheath 52, located at the working head 22. A needle 54 is slideably disposed at the distal end of the injection sheath 52. The needle may be a 23 gauge needle. In a retracted position, as illustrated by FIG. 6B, the needle 54 is disposed completely within the injection sheath 52. The needle 54 may be slid to an extended position (not shown) in which the needle 54 extends a specified distance out of the distal end of the injection sheath 52. It is contemplated that a plurality of needles, such as a needle array, may be disposed at the distal end of the injection sheath 52. Alternatively, a needle 54 or the plurality of needles may be retractably disposed at the working head 22.

Referring to FIGS. 12 A-B, the polygonal manipulator device 10 may be precisely and accurately controlled using an electronic control system 56. The control system includes a housing 58, a microcontroller (not shown), such as an Arduino Mega 2560, continuous-rotation servos 62, and encoders 64 for positioning feedback. In the depicted embodiment, three-servos 62 and three encoders 64 are used. It is understood however, that in those configurations that employ more than three cables, more than three servos 62 and encoders 64 may be necessary. Each servo 62 rotates a bobbin 66 which in turn tensions a corresponding cable 230. Control may be performed using position feedback as the output and servo speed as the input. An independent proportional-integral-derivation (PID) loop is run for each servo. For example, three independent PID loops may run at 1000 Hz. Optionally, the control system 56 may include a graphical user interface (GUI), such as a computer, to allow the surgeon to control the device remotely. Although it is understood that any user interface or interface device configured to allow the surgeon to interact with the control system 56 may be used. Due to the flexibility of the flexure arms 14 and 15, the deployed geometry of the polygonal manipulator device 10 may vary in an unpredictable operating environment. To account for this, geometric homing is performed. The encoders 64 measure differential lengths of the cables. By calculating the difference in a value of the encoder 64, changes in cable length may be determined.

In another embodiment the control system 56 may include a pump (not shown) located at the proximal end of the injection sheath 52. The pump may be fluidly connected to the conduit of the injection sheath to propel an injection fluid through the conduit and into the needle 54 for injection.

Injection of the needle 54 may be controlled manually, although it is contemplated that injection and deployment of the needle would typically be controlled using a computer control system 56. It is noted that deployment of the needle 54 may be achieved using various actuation mechanisms, for example, a push-pull solenoid actuator, a geared actuator with a servo motor, a pneumatic actuator can be used to cause extension and retraction of the needle 54.

Figure 10A:
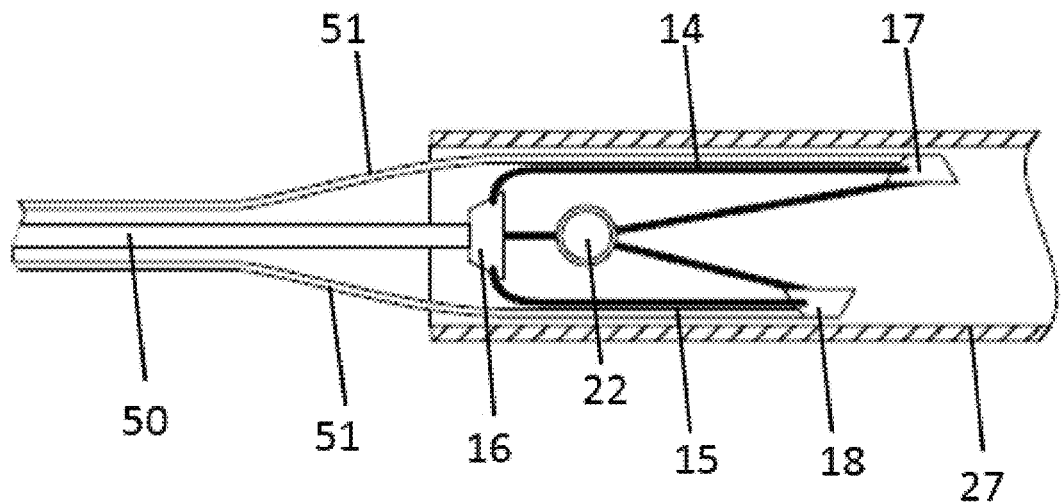
FIG. 10A is a cross-sectional view of a cannula as a polygonal manipulator device, e.g., of FIG. 1, is being deployed through the cannula, with introducer arms attached to the device.
Figure 10B:
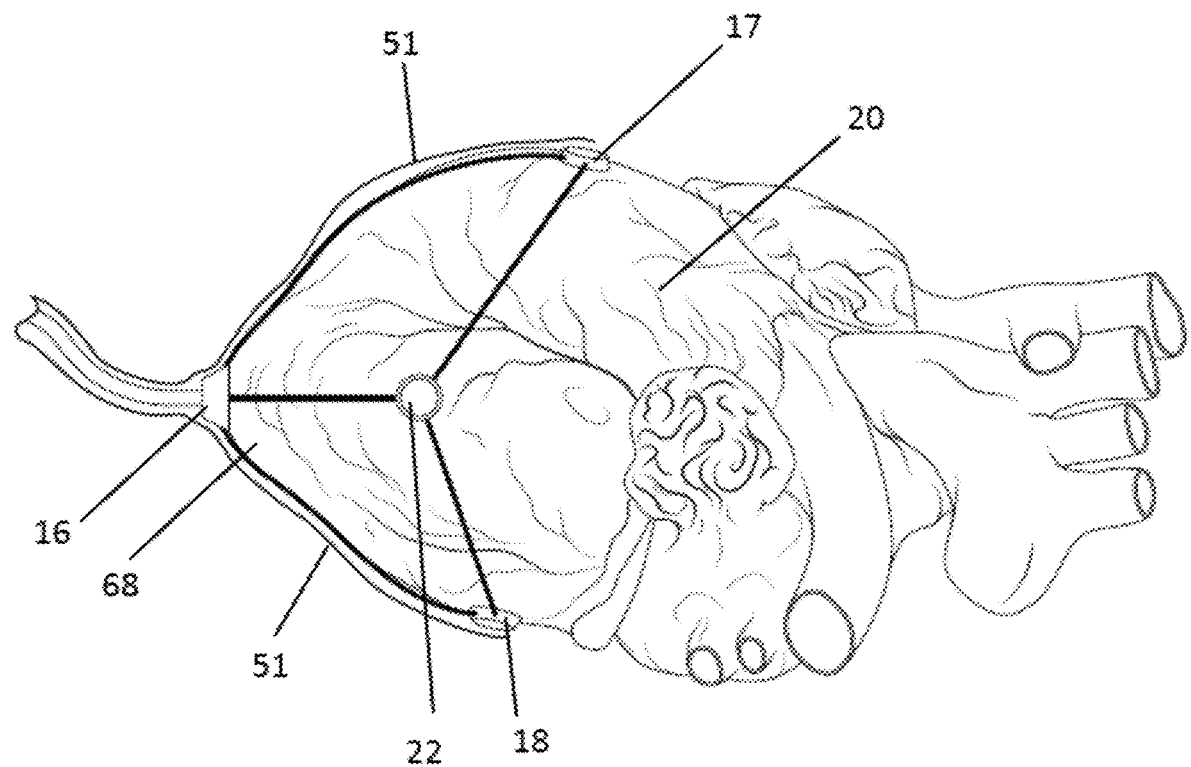
FIG. 10B is a perspective view of the deployable polygonal manipulator device, e.g., of FIG. 1, with the device attached to the heart and the introducer arms attached to the device.

In one embodiment, as shown by FIG. 10A, introducers 50 and 51 may be secured to either permanently or detachably secured via a quick-disconnect fitting, to each of the proximal 16 and distal suction bases 17 and 18. The introducers 50 and 51 may be detachably secured to the suction bases for easy removal after the suction bases 16, 17 and 18 are positioned. The introducers 50 and 51 may be any structure, of any material, such as a metal alloy or polymeric composition useful in positioning the suction bases 16, 17 and 18, such as, without limitation rods, tubes, guide wires, and elongated, flattened metal or polymeric strips with a rectangular cross-section, that is, having a width significantly greater (e.g., at least 2-, 5-, 10-, 20-fold) than a thickness, such that the depicted introducers 51, which are substantially flexible in a plane defined by a length or longitudinal axis and a first axis perpendicular to the longitudinal axis, but are substantially rigid side-to-side, in a second plane defined by the longitudinal axis and an axis perpendicular to both the first axis and the longitudinal axes, thereby allowing the distal bases 17 and 18 to slide along a surface of the heart 16, as is shown in FIG. 10B, but being stiff enough in a longitudinal and perpendicular direction to facilitate positioning of the distal bases 17 and 18. Analogous structures to polymeric strips useful as introducers are cable ties, also known as zip ties.

The polygonal manipulator device 10 is designed so that it may be inserted into a cannula 27, such as a 20-mm cannula (when the flexure arms 14 and 15 are in a collapsed state), as shown in FIG. 9, to access the heart in a minimally invasive manner. To use the manipulator device, a small incision is made beneath the xyphoid process of the sternum. The cannula 27 is then inserted through the incision and the manipulator device is deployed from the cannula 27 and onto the heart 20 under the pericardium by pushing on the proximal end of the manipulator device 10. After deployment, the flexure arms 14 and 15 expand according to any mechanism, such as one of the passive or active mechanisms disclosed above. The surgeon manually positions the support structure 12, so that the entirety of the intervention site is located inside an area defined by the plurality of suction bases 16, 17 and 18. In one embodiment, the stiffness of the flexure arms 14 and 15 allow the device to further expand passively so that the flexure arms 14 and 15 spread as the arms slide onto the heart 20, obviating the need for springs and/or active actuators. In another embodiment, as shown in FIG. 10B, the introducer arms 50 and 51, being highly flexible in only one plane will facilitate the positioning of the distal suction bases 17 and 18 by guiding the bases over the surface of the heart 20 after the surgeon places the proximal suction base 16 on the apex 68 of the heart as shown in FIG. 10B.

Figure 10C:
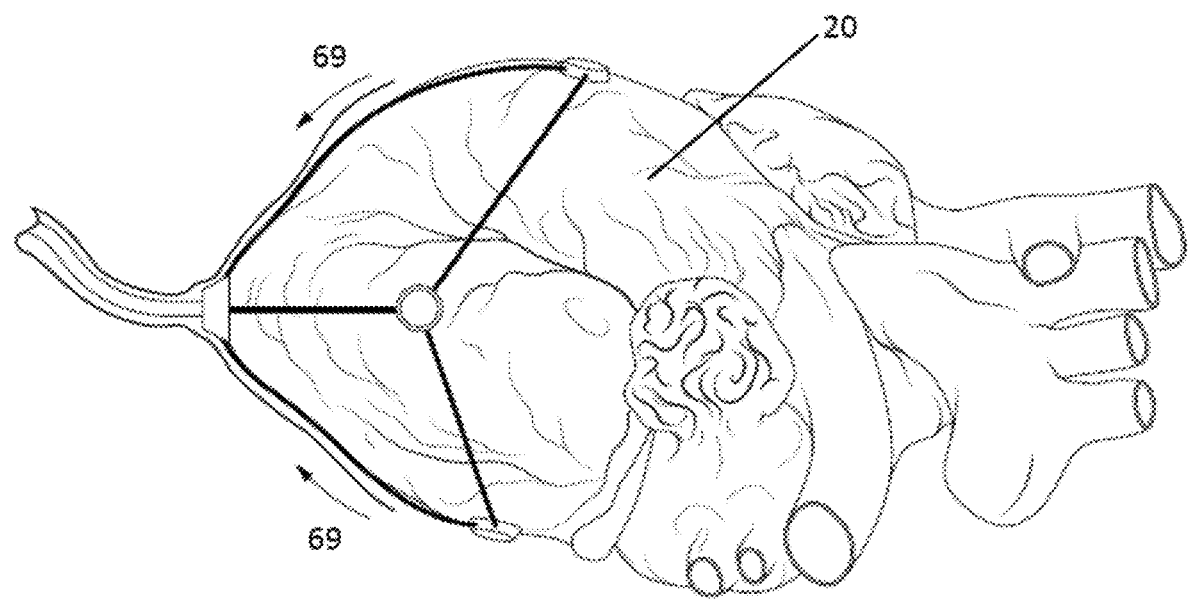
FIG. 10C is a perspective view of the deployable polygonal manipulator device, of FIG. 1, with the device attached to the heart as the introducer arms released from the device.

Once positioned, the vacuum source is activated, thereby providing a negative pressure to the vacuum chambers 23 of the suction bases via the vacuum lines. The negative pressured suction force at the vacuum chambers 23 located at an open end of the suction bases 16, 17 and 18 allows the suction bases to adhere to a smooth surface of an organ. When the suction bases 16, 17 and 18 are adhered to the surface of the heart 20, the support structure 12 of the device 10 moves in unison with the periodic beat of the heart 20. Thus, therapies may be provided from a zero relative motion perspective. With reference to FIG. 10C, after the suction bases are adhered in position, the introducers 50 and 51 may be disconnected and pulled in direction 69 towards the proximal end 34 of the cannula 27.

Figure 12A:
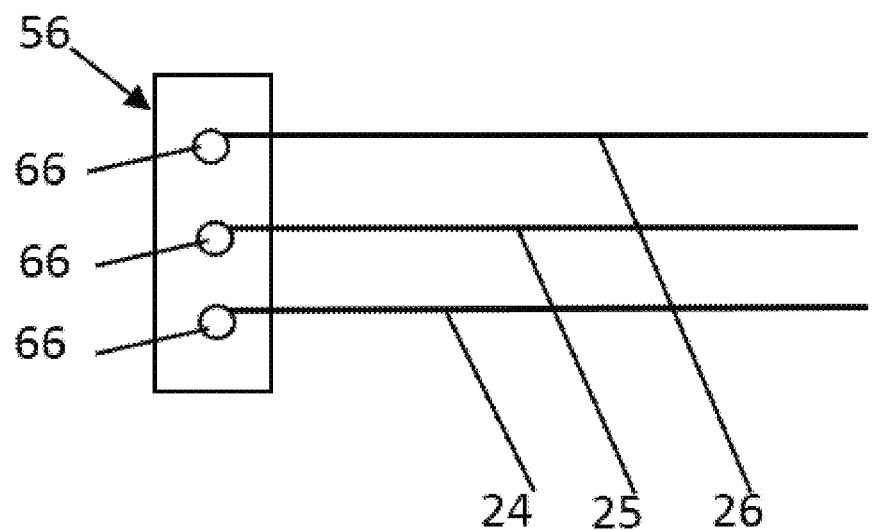
FIG. 12A is top-view of a schematic drawing of a cable control system for use in a system as described herein.
Figure 12B:
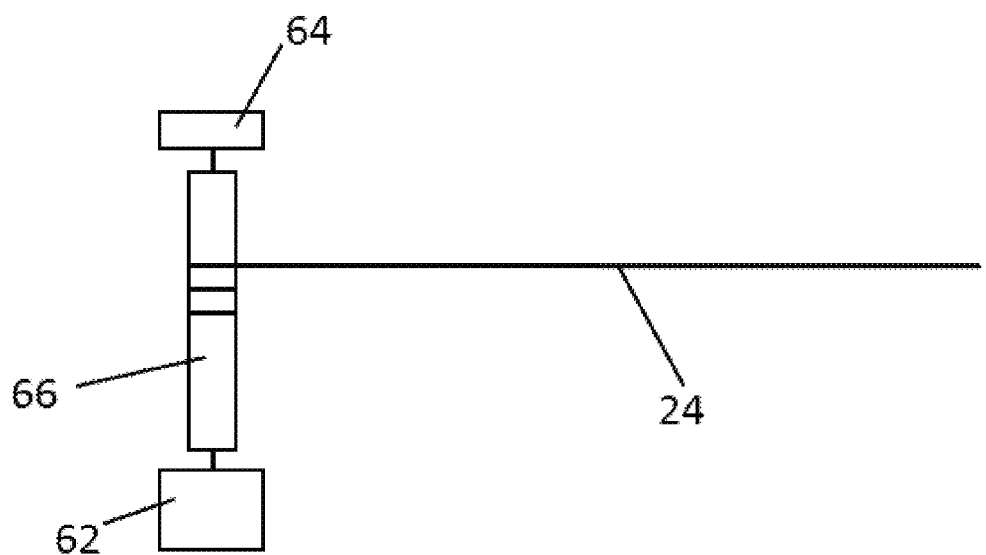
FIG. 12B is a side view of a schematic drawing of a single unit of the cable control system shown in FIG. 12A, for controlling a length of each cable of a system as described herein.

Positioning of the working head 22 to perform any of the therapies previously discussed can be controlled in several manners. The positioning may be controlled via the control system 56 in a semi-autonomous mode where the clinician identifies the locations where interventions are required on preoperative models of the heart 20 and the control system 56, as described, rotates the bobbin 64 to tensions its corresponding cable 20, as illustrated in FIG. 12A. With reference to FIG. 12B, a plurality of bobbins, where one bobbin corresponds to each cable may be used to elongate and or tighten the corresponding cable. As a result the working head 22 can be positioned in any location within a boundary defined by the plurality of suction bases 16, 17 and 18. The semi-autonomous mode of operation is advantageous in performing procedures that may require many discrete interventions, such as injections, over a relatively large area, as well as continuous interventions along a continuous line or arc, such as ablation. The semi-autonomous module utilizes the clinician's expertise in identifying intervention sites, but allows for the working head 22 to automatically position itself according to a module, thus positioning of the working head may be achieved quickly and accurately so that any of the previously discussed interventions may be performed.

FIGS. 13A and 13B provide simplified schematic diagrams of one non-limiting embodiment of a device as described herein. In FIGS. 13A and 13B, a device 310 comprising arms 314 and 315, suction bases 316, 317 and 318, and a cannula 327 for delivery of the device 310. The arms 314 and 315 can be rigid or flexible. The arms 314 and 315 join and are hinged at suction base 316. Beam 335 is attached to a distal end of arm 314 in a hinged manner permitting rotation of the beam 335. When the device is in the cannula 327 and is initially deployed it is in a delivery configuration as shown in FIG. 13A, and arms 314 and 315 are separated as shown by arrows in FIG. 13A. For deployment, the end of the beam 335 opposite the hinged attachment to arm 314 is moved to an attachment point 336, as shown in FIG. 13B, where it is releasably affixed to arm 315 at the attachment point by any fastener or quick release. Any manipulator, such as an introducing element as described above, can be used to move the beam 335 into place for deployment and subsequently unfasten the beam 335 from arm 315 for retrieval of the device 310. Suitable hinge structures and fastener structures are known in the art and need not be described in detail to appreciate this particular embodiment.

During in vivo use, it is also contemplated, that various visualization methods, such as an endoscopic camera, e.g., a suitable charge-coupled device (CCD) and lens combination, with optional lighting from, e.g. an LED or fiber optic cable, ultrasound or fiberscopes may be used. Additional visualization techniques such as fluoroscope could alternatively or additionally be used to provide real-time medical imaging information to the clinician during the surgical intervention. To facilitate visualization of the device in use, radiopaque materials/markers, as are broadly known in the medical arts, for example for positioning stents, may be incorporated into one or more elements of the device described herein, such as in the working head and/or in one or more of the suction bases.

Example

The device and system tested was essentially as depicted and described in relation to FIGS. 1-9 and 12, as described above.

Device Design

A prototype epicardial wire robot was prepared essentially as shown in FIG. 2. The device consists of the two distal suction bases and a proximal suction base built using rapid prototyping techniques. The two arms connecting the left and right distal bases to the proximal base are made of neoprene tube, through which Tygon® suction lines and PTFE sheaths for the drive cables are delivered to the distal bases.

The prototype relies on the compliance of the arms to allow the device to passively fold to fit within the delivery cannula, and, upon exiting, to return to the deployed state. The compliance in the arms also allows the device to attach to a curved surface at the three base locations. The position of the injection head can be adjusted by pulling on the three drive wires which run from the head to each base, through the PTFE sheaths in the flexure arms, and out of the proximal base. The drive wires in the current prototype consist of braided fishing line. The longer arm is 100 mm long, and the shorter arm 75 mm.

Kinematics

For motion and path planning a planar approximation has been made. Because the device is a parallel manipulator, no closed form solution exists for the forward kinematics. However, the planar approximation means that the inverse kinematics can be solved by drawing a circle concentric to each base and finding the radius of each circle when they all intersect at the same point, as shown in FIG. 11. This represents the Euclidean distance between the points.

Planning algorithms have been developed that will allow surgeons to draw a path or a series of injection sites, to which the manipulator can autonomously travel under minimum-jerk trajectory conditions. The inverse kinematics means that by using the robot Jacobian, the Cartesian coordinate space can be directly translated into the coordinate space of the robot. The geometry of the device yields the inverse kinematics:

$$\begin{bmatrix} r_l \\ r_r \\ r_m \end{bmatrix}^2 = \begin{bmatrix} [x_0 + L_l\cos(\theta_l)]^2 + [y_0 - L_l\sin(\theta_l)]^2 \\ [x_0 + L_r\cos(\theta_r)]^2 + [y_0 - L_r\sin(\theta_r)]^2 \\ x_0^2 + y_0^2 \end{bmatrix}$$

Cardiac Access

The device is designed to access the heart in a minimally invasive way by utilizing a subxiphoid approach. After subxiphoid access is created and an incision is made in the pericardium, the manipulator is inserted into a 20-mm cannula. This cannula is inserted into the hole, and by pushing on the back end of the manipulator, it is deployed onto the heart under the pericardium. The stiffness of the arms allows the robot to passively open on the heart, obviating onboard motors or springs.

Once deployed onto the heart, suction is turned on to secure the manipulator to the heart. The tether for the injection head slides freely in the main base, allowing the surgical tool to be moved rapidly anywhere within the workspace. Injection is performed manually.

Electronic Control System

In order to provide precise and accurate control of the tool, an electronic control system has been developed, essentially as depicted schematically in FIG. 5. The low-level control system includes an Arduino Mega 2560 microcontroller, three continuous-rotation servos, and three encoders for position feedback.

Control is performed using only position feedback as the output and servo speed as the input. Three independent PID loops run at 1000 Hz. The PID controllers were independently tuned by first estimating a transfer function numerically using MATLAB's System Identification Toolbox and then using the function "pidtune" to tune for a unit step function input. The control system has a graphical user interface (GUI) that allows the surgeon to control the device remotely.

Geometric Homing

Due to the flexibility of the arms, the deployed geometry of the device can vary due to the unpredictable operating environment. In order to account for this, geometric homing is done using the encoders which measure differential wire length. In the homing procedure, the tool head is moved manually to each base, in sequence. By calculating the difference in encoder values, the changes in cable lengths are determined, allowing for recovery of the deployed device geometry.

Movement of the injection head, suction, and injection have been tested in vitro. The device was first tested on a balloon coated in lubricant with a stocking pulled over it to simulate the heart and pericardium. Prototypes that demonstrated successful suction and movement of the injector head were then tested for injection into animal muscle tissue ex vivo. In all, 16 prototypes were tested.

The manipulator was then tested in vivo in a porcine model (N=3) under a board-approved protocol. The device was inserted using subxyphoid access and tested for movement of the injection head, injection of ink, suction, and visualization under fluoroscope.

Testing In Vitro

No prototypes had difficulty adhering to the balloon or chicken breast during testing in vitro. Initial difficulties were overcome in movement of the injection head. Rotation of the tether sometimes caused the head to rotate as well. Redesign to relocate the anchor positions for the strings allowed for the rotational moment to be minimized Ink injection into the chicken tissue was performed and deemed successful at a depth of 5 mm.

Geometric Homing

Benchtop tests were conducted to ensure that the geometric homing procedure provided accurate results. Because two measurements are made for each string length (i.e., as one string shortens, another lengthens when going from one base to another), comparing the two measurements allowed verification. Measurements within 5% of each other were considered accurate. Use of these measurements quantifies the size of the robot, and then rotation of the axes is chosen, as previously described and as seen in FIG. 11, letting $\theta_1 = \theta_r$ to simplify calculations. During tabletop testing, the length of the left and right sides of the workspace were measured via geometric homing as 80.1 mm and 61.9 mm respectively, while the actual dimensions were 83 mm and 62 mm, corresponding to errors of 3.5% and 0.2%, respectively.

Testing In Vivo

Insertion and Deployment

Figure 14:
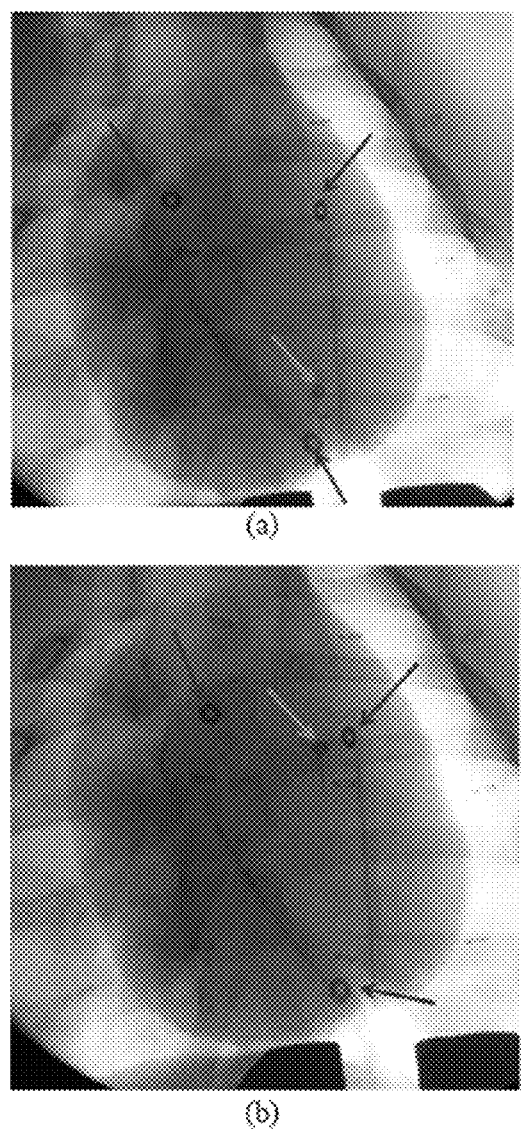
FIG. 14 provides two fluoroscopic views of the manipulator deployed in a porcine model in vivo, with washers affixed to the three suction chambers and the end-effector head for radiopacity. Dark gray arrows show suction chambers, light gray arrows shows the injection head. (a) The end-effector near the main base (bottom of the "V"). (b) The end-effector near the right base (right tip of the "V").

The manipulator was successfully inserted and deployed via subxiphoid access and a small incision in the pericardium near the apex of a heart of a pig. Images from before and after the insertion were obtained (FIG. 14). During insertion, the device was collapsed inside the cannula, and the cannula was inserted into the pericardial space. The device was advanced through the cannula to the surface of the heart. As the device exited the cannula, the flexible arms expanded to the deployed state and suction was provided to the bases to adhere to the surface of the heart. In some cases, there was some error in the positioning, because twisting can occur under deployment, thus hindering suction if the vacuum lines twist. The pericardium helps fix this problem, by applying a reactive force onto the device facilitating static equilibrium.

With the device adhered to the anterior surface of the heart, geometric homing was performed using the electronic control system as described. The working head was moved to each suction base and viewed under fluoroscope to ensure the correct position. Using a computer, the injection head was then moved to each base and injections were performed. A sternotomy revealed the device deployed under the pericardium and the working head was moved to ensure that electronic control was achieved. Inspection of the device and surface of the heart showed that there was no obstruction of the suction heads due to aspiration of liquid or debris. Upon excision of the heart, two injection sites were identified.

Tool Head Motion

Fluoroscopy was used to visualize the device during operation. Small stainless steel washers were embedded in each suction base, as well as the working head, to aid in visualization. During operation the GUI was used to position the injection head at various locations in the reachable workspace. After deployment onto the heart, images and video were captured on the fluoroscope demonstrating the motion capabilities of the manipulator. The injection head moved easily under the pericardium.

Injections

During each procedure, injection into the myocardium was demonstrated. For each injection the tool head was moved to the edge of the robot workspace and a PTFE lumen with a 23 gauge needle tip was advanced through a PTFE sheath embedded in the tool head approximately 5 mm. Water-based ink (0.1 mL) was injected into the myocardium, allowing injections to be identified post-operatively.

Upon completion of the intervention, the polygonal manipulator device was removed by turning off the vacuum source to release the suction bases from the heart. The device was collapsed into the cannula by pulling the device into the cannula. The pig heart was excised, and ink injections were observed on the heart's surface.

The epicardial wire robot manipulator successfully demonstrated insertion, deployment, tool manipulation, and injection in vivo. Additional modifications to the device include:

i. Accommodation for an electromagnetic tracker, enabling registration to preoperative models and intraoperative image guidance.

ii. Reducing size while maintaining suction force, surgical tool movement, and injection capability. Initial prototypes have featured neoprene rubber arms for stiffness. Sheaths with thinner walls and smaller outer diameter are being considered in order to reduce the size of the bases.

iii. The vacuum chambers can also be reduced. Initially, the chambers were generously sized in order to ensure adhesion, but new refinements will measure adhesion and scale the chambers accordingly.

iv. Injection depth is currently manually controlled to about 5 mm. While manual injection has been relatively successful, future versions will automate injection depth to ensure consistency.

While the disclosure has been described having exemplary designs, the present disclosure can be further modified within the spirit and scope of this disclosure. This application is therefore intended to cover any variation, use, or adaptations of the disclosure using its general principles. Further, this application is intended to cover such departures from the present disclosure as come within known or customary practice in the art to which this disclosure pertains and which fall within the limits of the claims.

We claim:

1. A deployable manipulator device for surgical interventions configured to transition between a delivery configuration and a deployment configuration, the device comprising:

at least three suction bases, each comprising a chamber, a first opening and a second opening, wherein a distance between at least two suction bases is greater in the deployment configuration as compared to the delivery configuration;

at least one vacuum line extending from the second openings of the suction bases configured to apply a vacuum to the chambers for attaching the suction bases to a surface;

at least three cable guides configured to be positioned at three non-collinear points when the device is in the deployment configuration, wherein a distance between at least two of the cable guides is greater in the deployment configuration as compared to the delivery configuration;

a head for supporting a surgical tool; and at least three cables, wherein each of the at least three cables is connected to the head and passing through a different one of the three cable guides, wherein, with the at least three suction bases attached to the surface, the cables cooperatively extend from the retract through the cable guides to control a position of the head over the surface within an area delimited by the at least three suction bases, wherein extension of at least one of the at least three cables through one of the cable guides and retraction of a different one of the at least three cables through another of the cable guides moves the head over the surface towards at least one of the at least three suction bases within the area delimited by the at least three suction bases.

2. The device of claim 1, further comprising:
at least two support arms each comprising a proximal end connected to a connector and a distal end opposite the proximal end, wherein the support arms can be manipulated between the delivery configuration and the deployment configuration where distal ends of the arms are separated by a greater distance in the deployment configuration,
wherein at least two of the suction bases are attached to different support arms so that a distance between the at least two suction bases located on different support arms is greater in the deployment configuration as compared to the delivery configuration, and
wherein at least two of the cable guides are attached to different support arms so that a distance between the at least two cable guides located on different support arms is greater in the deployment configuration as compared to the delivery configuration.

3. The device of claim 2, wherein the at least two support arms are made from a flexible material or a resilient material.

4. The device of claim 3, in which the at least two support arms are resilient.

5. The device of claim 3, in which the the at least two support arms are flexible, the device further comprising an elongate member attached to one or more of the at least three suction bases to facilitate deployment of the device.

6. The device of claim 5, each of the at least two support arms having a length extending from a distal end of the support arm to a proximal end of the support arm, wherein at least one of the at least three support arms has greater flexibility along its length in one direction as compared to a direction perpendicular to the one direction.

7. The device of claim 2, further comprising at least one spring disposed at a joint located between the at least two support arms to bias at least a portion of the plurality of two support arms apart from one another.

8. The device of claim 2, wherein the at least three suction bases are triangularly spaced apart when the at least two support arms are in the deployed configuration.

9. The device of claim 1, in which at least one of the at least three cable guides are integral with one of the at least three suction bases.

10. The device of claim 1, in which the at least three suction bases include a proximal suction base and a plurality of distal suction bases, wherein each of the distal and proximal suction bases comprise one of the at least three cable guides through which one of the at least three cables passes.

11. The device of claim 10, comprising an elongate member attached to the proximal base and to each of the distal bases to facilitate deployment of the device.

12. The device of claim 1, further comprising a vacuum source connected to the at least three suction bases by a vacuum line fluidly connecting the vacuum source to each of the at least three suction bases.

13. The device of claim 1, further comprising a detachable elongate member secured to at least one of the at least three suction bases to facilitate deployment of the device.

14. The device of claim 13, in which the detachable elongate member comprises is a rod, tube, guide wire, or one or more flat, elongated metal or polymer strips bending in substantially only one plane.

15. The device of claim 1, further comprising an electromagnetic positioning sensor.

16. The device of claim 1, further comprising a camera, an ultrasound probe and/or a fiberscope.

17. The device of claim 1, wherein the head comprises an injector comprising at least one retractable needle.

18. The device of claim 17, wherein the head comprises a plurality of retractable needles.

19. The device of claim 1, wherein the head comprises a tissue ablator.

20. The device of claim 19, wherein the tissue ablator is a mechanical, laser, or radiofrequency ablator.

21. A method for performing a surgical intervention using a manipulator device, the method comprising:
i. introducing the device of claim 1 into a patient through an incision;
ii. positioning the support structure of the device over a location of a target organ;
iii. attaching the support structure to the target organ by applying a vacuum to the suction bases;
iv. positioning the working head over an intervention site located at the location of the target organ;
v. performing the surgical intervention using the working head; and
vi. retrieving the device upon completion of the surgical intervention.

22. The method of claim 21, further comprising monitoring movement of the working head using a real-time medical imaging method.

23. The method of claim 22, wherein the real time medical imaging technique comprises fluoroscopy.

24. A system for performing a surgical intervention comprising:
i. The deployable manipulator device of claim 1
ii. a vacuum source to provide negative pressure to the at least three suction bases;
iii. an electronic control system for at least controlling the positioning of the working head; and
iv. an actuator to control the positioning of the working head by independently controllably pulling or releasing each of the cables, thereby positioning the working head.

25. The system of claim 24, wherein the plurality of support arms are made from a flexible material or a resilient material.

26. The system of claim 25, in which the plurality of support arms are resilient.

27. The system of claim 25, in which the plurality of support arms are flexible and the device further comprises an introducer attached to one or more of the suction bases.

28. The system of claim 27, each of the support arms having a length extending from a distal end of the support arm to a proximal end of the support arm, wherein at least one of the support arms has greater flexibility along its length in one direction as compared to a direction perpendicular to the one direction.

29. The system of claim 24, further comprising at least one spring disposed at a joint located between the plurality of support arms to bias at least a portion of the plurality of support arms apart from one another.

30. The system of claim 24, wherein the support structure includes three suction bases that are triangularly spaced apart when the support arms are in the deployed configuration.

31. The system of claim 24, in which at least one of the cable guides are integral with a suction base.

32. The system of claim 24, further comprising a vacuum source connected to the at least three suction bases by a vacuum line fluidly connecting the vacuum source to each of the at least three suction bases.

33. The system of claim 24, further comprising a detachable introducer element secured to one of the at least three bases.

34. The system of claim 33, in which the introducer element is one or more flat, elongated metal or polymer strips bending in substantially only one plane.

35. The system of claim 24, further comprising an electromagnetic positioning sensor.

36. The system of claim 24, further comprising a camera, an ultrasound probe or a fiberscope.

37. The system of claim 24, further comprising an interface device for controlling the working head.

38. The system of claim 24, wherein the working head comprises an injector comprising at least one retractable needle.

39. The system of claim 24, wherein the working head comprises a plurality of retractable needles.

40. The system of claim 24, wherein the actuator comprises a plurality of bobbins around which proximal ends of the cables are wrapped, wherein the bobbins are connected to a servo motor, and the cables are pulled or released by rotation of the bobbins.

* * * * *

UNITED STATES PATENT AND TRADEMARK OFFICE
CERTIFICATE OF CORRECTION

PATENT NO. : 10,736,703 B2
APPLICATION NO. : 14/725848
DATED : August 11, 2020
INVENTOR(S) : Nathan Wood et al.

Page 1 of 1

It is certified that error appears in the above-identified patent and that said Letters Patent is hereby corrected as shown below:

In the Claims

Column 16, Line 61, Claim 1, delete "passing" and insert -- passes --

Column 16, Line 64, Claim 1, delete "from the" and insert -- from and --

Column 17, Line 32, Claim 5, delete "the the" and insert -- the --

Column 17, Line 36, Claim 6, before "each" insert -- wherein --

Column 17, Line 37, Claim 6, delete "having" and insert -- has --

Column 17, Line 38, Claim 6, before "wherein" insert -- and --

Column 17, Line 44, Claim 7, delete "plurality of" and insert -- at least --

Column 17, Line 50, Claim 9, delete "are" and insert -- is --

Column 17, Line 52, Claim 10, after "which" insert -- each of --

Column 17, Line 53, Claim 10, delete "include" and insert -- includes --

Column 18, Line 2, Claim 14, after "comprises" delete "is"

Signed and Sealed this
Twelfth Day of January, 2021

Andrei Iancu
*Director of the United States Patent and Trademark Office*